(12) United States Patent
Suuronen et al.

(10) Patent No.: US 8,861,679 B2
(45) Date of Patent: Oct. 14, 2014

(54) X-RAY IMAGING SYSTEMS AND METHODS (75) Inventors: Esa Suuronen, Kerava (FI); Tero Isoaho, Tuusula (FI); Juha Matikainen, Vantaa (FI); Andreas Melin, Espoo (FI); Douglas Woods, Franklin, WI (US); Jari Joutsela, Nurmijarvi (FI)

(73) Assignee: PaloDEx Group Oy, Tuusula (FI)

( * ) Notice: Subject to any disclaimer, the term of this patent is extended or adjusted under 35 U.S.C. 154(b) by 621 days.

(21) Appl. No.: 13/113,714

(22) Filed: May 23, 2011

(65) Prior Publication Data

US 2011/0305320 A1 Dec. 15, 2011

Related U.S. Application Data (60) Provisional application No. 61/353,975, filed on Jun. 11, 2010.

(51) Int. Cl.
   - *H05G 1/64* (2006.01)
   - *A61B 6/00* (2006.01)
   - *A61B 6/04* (2006.01)
   - *A61B 6/14* (2006.01)

(52) U.S. Cl.
   CPC . *A61B 6/00* (2013.01); *A61B 6/469* (2013.01); *A61B 6/467* (2013.01); *A61B 6/542* (2013.01); *A61B 6/463* (2013.01); *A61B 6/14* (2013.01); *A61B 6/0478* (2013.01); *A61B 6/488* (2013.01)
   USPC ........................................................ 378/98.5

(58) Field of Classification Search
   CPC ........................................................ A61B 6/14
   USPC ....................... 378/38, 37, 62, 162–166, 98.5
   See application file for complete search history.

(56) References Cited

U.S. PATENT DOCUMENTS 5,416,819 A * 5/1995 Uzuyama et al. ............. 378/116
6,049,584 A   4/2000 Pfeiffer (Continued)

FOREIGN PATENT DOCUMENTS

| CN | 1644165 | 7/2005 |
|---|---|---|
| CN | 1874726 | 12/2006 |

(Continued)

OTHER PUBLICATIONS

European Patent Office Communication for corresponding application EP 11 16 9636, dated Apr. 17, 2013.

(Continued)

*Primary Examiner* — Irakli Kiknadze
(74) *Attorney, Agent, or Firm* — Andrus Intellectual Property Law, LLP (57) ABSTRACT

X-ray imaging systems and methods utilize an imaging apparatus comprising an emitter emitting X-rays through an object and a receiver receiving the X-rays. A control circuit controls the emitter and processes the X-rays received by the receiver to generate X-ray images of the object. The control circuit controls a display to display an initial view of the object, the display of the initial view being modifiable by a user; controls the imaging apparatus to generate an X-ray positioning image of the object based upon a user modification of the display of the initial view; controls the display to display the positioning image, the display of the positioning image being modifiable by a user; and controls the imaging apparatus to generate an X-ray image of the object based upon a user modification of the display of the positioning image.

32 Claims, 10 Drawing Sheets

(56) References Cited

U.S. PATENT DOCUMENTS

| | | | |
|---|---|---|---|
| 6,118,842 | A | 9/2000 | Arai et al. |
| 6,619,839 | B2 | 9/2003 | Yoshimura |
| 7,170,968 | B2 * | 1/2007 | Sukovic .......... 378/20 |
| 7,711,085 | B2 | 5/2010 | Suzuki et al. |
| 7,929,661 | B2 * | 4/2011 | Borghese et al. ....... 378/38 |
| 7,991,107 | B2 | 8/2011 | Sadakane et al. |
| 2005/0157840 | A1 | 7/2005 | Gohno et al. |
| 2009/0168966 | A1 | 7/2009 | Suzuki et al. |
| 2009/0238329 | A1 | 9/2009 | Haras |
| 2009/0310741 | A1 | 12/2009 | Borghese et al. |
| 2009/0310845 | A1 | 12/2009 | Ogawa |
| 2010/0177865 | A1 | 7/2010 | Yoshimura |
| 2011/0064188 | A1 | 3/2011 | Suzuki et al. |

FOREIGN PATENT DOCUMENTS

| | | |
|---|---|---|
| EP | 0 197 227 A1 | 10/1986 |
| EP | 1 972 277 A1 | 9/2008 |
| WO | 2005/041775 A1 | 5/2005 |

OTHER PUBLICATIONS

European Search Report for corresponding application EP 11 16 9636, having a completion date of Sep. 16, 2011.

EP Communication—Office Action in corresponding EP Patent Application No. 11169636.5, dated Mar. 18, 2014.

Chinese Search Report and Office Action for Chinese Application No. 201110162613.1 dated Apr. 29, 2014.

* cited by examiner

X-RAY IMAGING SYSTEMS AND METHODS

CROSS-REFERENCE TO RELATED APPLICATION

The present application claims priority to and the benefit of U.S. Provisional Patent Application Ser. No. 61/353,975, filed on Jun. 11, 2010, the disclosure of which is hereby incorporated in entirety herein by reference.

FIELD

The present disclosure relates to X-ray imaging systems and methods.

BACKGROUND

U.S. Pat. No. 6,118,842 discloses a dual purpose X-ray imaging apparatus capable of partial CT imaging and panoramic tomographic imaging.

U.S. Pat. No. 6,619,839 discloses an X-ray object positioning apparatus for use in X-ray imaging apparatuses, wherein a relative positional relation between an object model and an imaging target area index, both displayed on a display, conforms with a relative positional relation between an object and an X-ray imaging target area moved by an imaging position moving apparatus.

U.S. Pat. No. 7,170,968 discloses a CT scanning system that includes a source and a detector mounted to a C-arm. A computer controls the rotation of a CT scanner and an X-ray source, and collects the data from the detector to create an image. The CT scanner first takes a scout scan prior to the full acquisition of the data. The scout scan is a single two-dimension image. The CPU draws locating marks on the scout scan image to indicate the desired location. When proper alignment is verified, the processor then controls the motor to perform one complete revolution of the C-arm, during which time the computer collects multiple images from the detector.

U.S. patent application Ser. No. 12/083,777 discloses a panoramic imaging apparatus which is able to freely display a focus-optimized internal structural image of the tooth row depending on a position using image data acquired by only one-time X-ray panoramic imaging from an arbitrary section along a patient's tooth row.

U.S. patent application Ser. No. 12/806,694 discloses a medical X-ray apparatus including a supporting part for supporting an X-ray generator and a two-dimensional X-ray detector while interposing an object to be examined therebetween, a radiation area restricting part for restricting a radiation area of X-ray generated from the X-ray generator, and a scan driving part for scanning the object with the X-ray restricted by the radiation area restricting part as X-ray beam and for executing radiography. A direction intersecting with X-ray scan direction is defined as a height direction. The apparatus further includes a radiation area setting part for setting at least one of both ends of width of the X-ray beam in the height direction at a desired position in accordance with the position of an interested area of the object. The X-ray beam is irradiated only to the radiation area as set by the radiation area setting part with its beam width in height direction restricted by the radiation area restricting part.

SUMMARY

The present disclosure results from the present inventors' research and development of improved X-ray imaging systems and methods. The inventors have realized that prior art X-ray systems and methods, including the systems and methods described herein above, often are not user friendly and can be inefficient and ineffective. The inventors have recognized that it is desirable to provide improved X-ray systems and methods that allow an operator to more easily and accurately identify an area of an object (e.g. an anatomical area of a medical or dental patient) for imaging, including for example 3-D imaging. The inventors have also recognized that it is desirable to provide improved X-ray systems and methods that limit excessive radiation to a patient being imaged. The inventors have realized that prior art X-ray systems and methods that display a single two-dimensional image from a preview scan do not provide an operator with all of the information necessary to take an accurate three-dimensional X-ray. This often results in inaccurate X-ray procedures, wasting time and applying excessive radiation to the patient.

The present disclosure provides X-ray systems and methods that overcome disadvantages in the prior art.

In one example, an X-ray imaging system comprises an imaging apparatus comprising an emitter emitting X-rays through an object and a receiver receiving the X-rays and a control circuit controlling the emitter and processing the X-rays received by the receiver to generate X-ray images of the object. The control circuit controls a display to display an initial view of the object, the display of the initial view being modifiable by a user; controls the imaging apparatus to generate an X-ray positioning image of the object based upon a user modification of the display of the initial view; and controls the display to display the positioning image, the display of the positioning image being modifiable by a user. Further, the control circuit controls the imaging apparatus to generate an X-ray image of the object based upon a user modification of the display of the positioning image.

The positioning image optionally comprises a plurality of X-ray images of the object from different angles. The plurality of X-ray images optionally are linked so that modification of one of the plurality of X-ray images on the display can cause corresponding modification of the rest of the plurality of X-ray images on the display.

The system optionally comprises a positioning position marker overlapping the positioning image. At least one of the positioning image and positioning position marker is modifiable with respect to the other of the positioning image and the positioning position marker and the control circuit controls the imaging apparatus to generate the X-ray image based upon a relative modification of the positioning image and positioning position marker. The modification optionally comprises a change in size and/or position of the positioning position marker and the control circuit controls the system to collimate an amount of X-rays emitted though the object based upon the size and/or position of the positioning position marker.

In another example, a method of operating an X-ray imaging apparatus comprising an emitter emitting X-rays through an object and a receiver receiving the X-rays comprises displaying an initial view of the object on a display; modifying the display of the initial view to identify a region of interest; operating, via the control circuit, the emitter and receiver to generate an X-ray positioning image of the object based upon the region of interest identified on the display of the initial view; displaying the positioning image on the display; modifying the display of the positioning image to further identify the region of interest; and operating, via the control circuit, the emitter and receiver to generate an X-ray image of the object based upon the region of interest identified on the positioning image.

In a further example, an X-ray imaging system comprises an imaging apparatus comprising an emitter emitting X-rays through an object and a receiver receiving the X-rays. A control circuit controls the emitter and processes the X-rays received by the receiver to generate X-ray images of the object. The control circuit controls the imaging apparatus to generate an X-ray positioning image of the object. The control circuit controls the display to display the positioning image, which is modifiable by a user. The positioning image comprises a plurality of X-ray images from the object from different angles that are linked such that modification of one of the plurality of X-ray images on the display can cause corresponding modification of the rest of the plurality of X-ray images on the display. The control circuit controls the imaging apparatus to generate an X-ray image of the object based upon a user modification of the display of the positioning image.

DETAILED DESCRIPTION OF THE DRAWINGS

In the present description, certain terms have been used for brevity, clearness and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. §112, sixth paragraph only if the terms "means for" or "step for" are explicitly recited in the respective limitation.

Figure 5A:
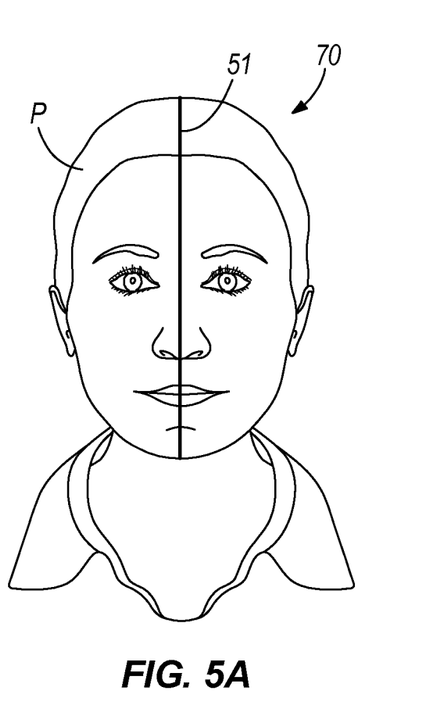
FIG. 5A is a view of migsagittal positioning lights.
Figure 5B:
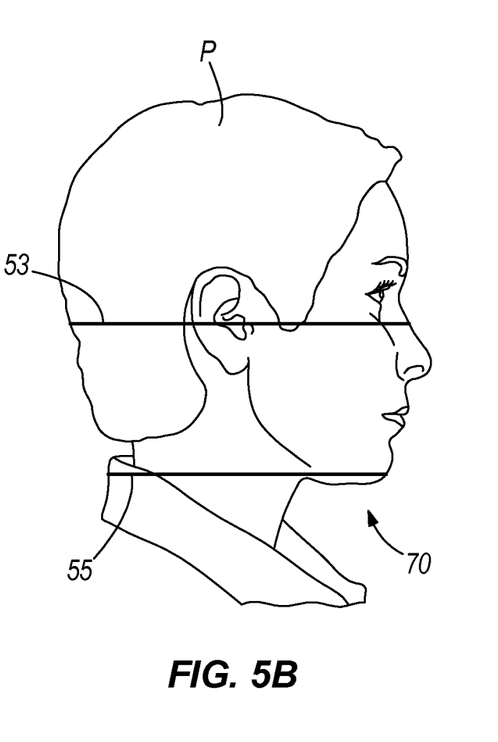
FIG. 5B is a view of horizontal positioning lights.

FIGS. 1A-1D depict an exemplary X-ray imaging apparatus 20 for acquiring X-ray images of an object, including for example a dental or medical patient P (see e.g., FIGS. 5A and 5B). In the particular example shown, the imaging apparatus 20 is configured for 3-D imaging of the dento-maxillofacial complex of the human skull; however other configurations of apparatuses for imaging of other portions of the object can instead be employed with the concepts of the present disclosure. The X-ray imaging apparatus 20 can optionally be configured to conduct different types of imaging procedures, for example panoramic imaging (for example standard, pediatric, ortho zone, wide arch, orthogonal, and/or the like), cephalometric imaging (for example cephalo pediatric lateral projection, cephalo lateral projection, cephalo postero-anterior, and/or the like), and/or 3-D imaging. The Figures depict just one example of an X-ray imaging apparatus for use with the concepts in the present disclosure. Other examples of X-ray imaging apparatus can instead be employed.

The imaging apparatus 20 has a housing 22 that is movably supported on a support column 24. The housing 22 can be moved up and down in the vertical direction V via a conventional guide motor (not shown) that is configured to move the housing 22 vertically up and down along a track 26 extending along support column 24. The housing 22 includes a generally vertically extending guide section 28 disposed on the support column 24 and a generally horizontally extending support section 30 extending generally horizontally from the guide section 28. The support section 30 supports a rotating section 32, which is rotatable in a horizontal plane H with respect to the stationary support section 30, as shown at arrow 34 in FIG. 1D. The support section 30 and/or rotating section 32 contain a conventional guide motor (not shown) configured to rotate the rotating section 32, as shown at arrow 34. In an alternate example, the apparatus can be mounted to a support structure including for example a wall instead of or in addition to being supported by a column.

An X-ray emitter housing 36 and an X-ray receiver housing 38 are opposed from each other and extend generally vertically from the rotating section 32. The emitter housing 36 contains an emitter generally located at 40 and supported in the emitter housing 36 and positioned to emit X-rays through the object being imaged (e.g. the patient P) to a receiver located at 42 and supported in the X-ray receiver housing 38. A patient positioning housing 44 extends from the guide section 28 and includes a chin support 48 for positioning the head of the patient P between the opposed emitter 40 and receiver 42. A head support 46 extends from the support section 30 through the rotating section 32. The chin support 48 and head support 46 are optional and other means for positioning the patient can be employed. A patient positioning panel 68 is located on the patient positioning housing 44 and receives user inputs for adjusting the position of various components of the imaging apparatus 20, as will be discussed further herein below.

A touch screen display 50 is attached to the housing 22 and is configured to receive user inputs for controlling the imaging apparatus 20 and to provide a display of functionalities of the imaging apparatus 20, as will be described further herein below. Optionally, the touch screen display 50 can be supported by an arm 49 that pivots about the imaging apparatus 20 for positioning in the positions shown in FIGS. 1A and 1B-D, respectively.

Figure 1A:
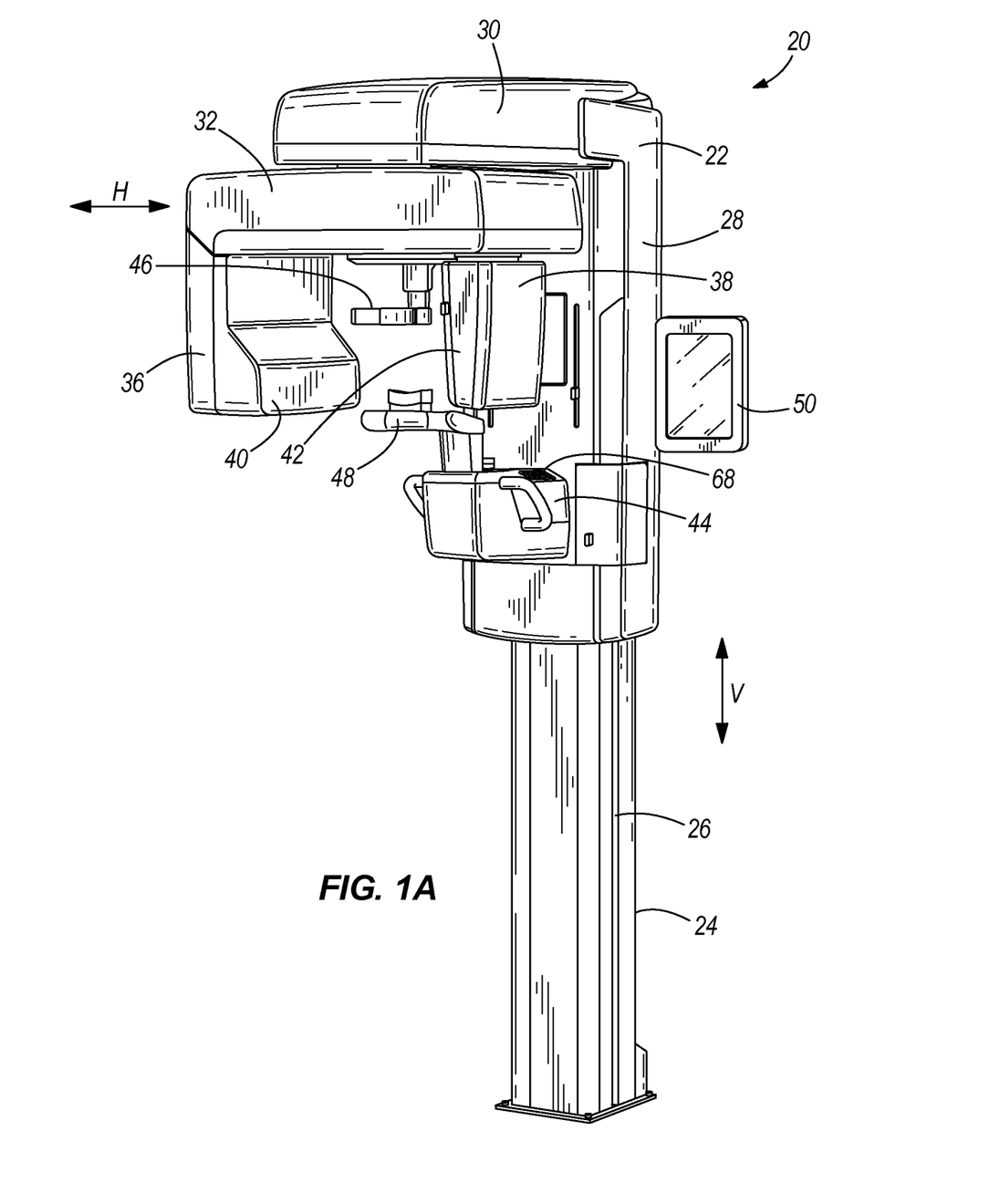
FIG. 1A is a perspective view of an exemplary X-ray imaging apparatus.
Figures 1B, 1C, 1D:
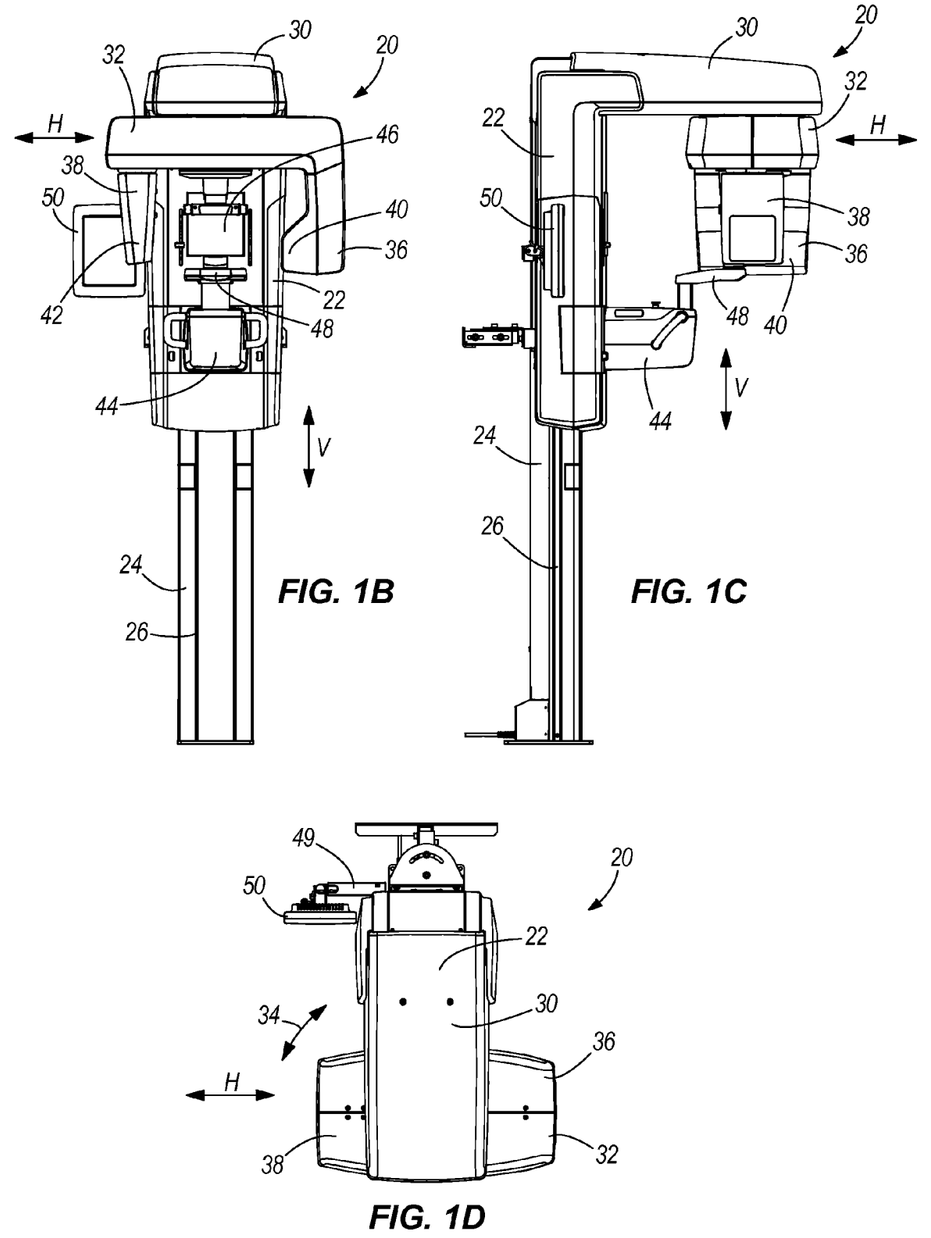
FIG. 1B is a front elevation view of the X-ray imaging apparatus.
FIG. 1C is a side elevation view of the X-ray imaging apparatus.
FIG. 1D is a top view of the X-ray imaging apparatus.
Figure 2:
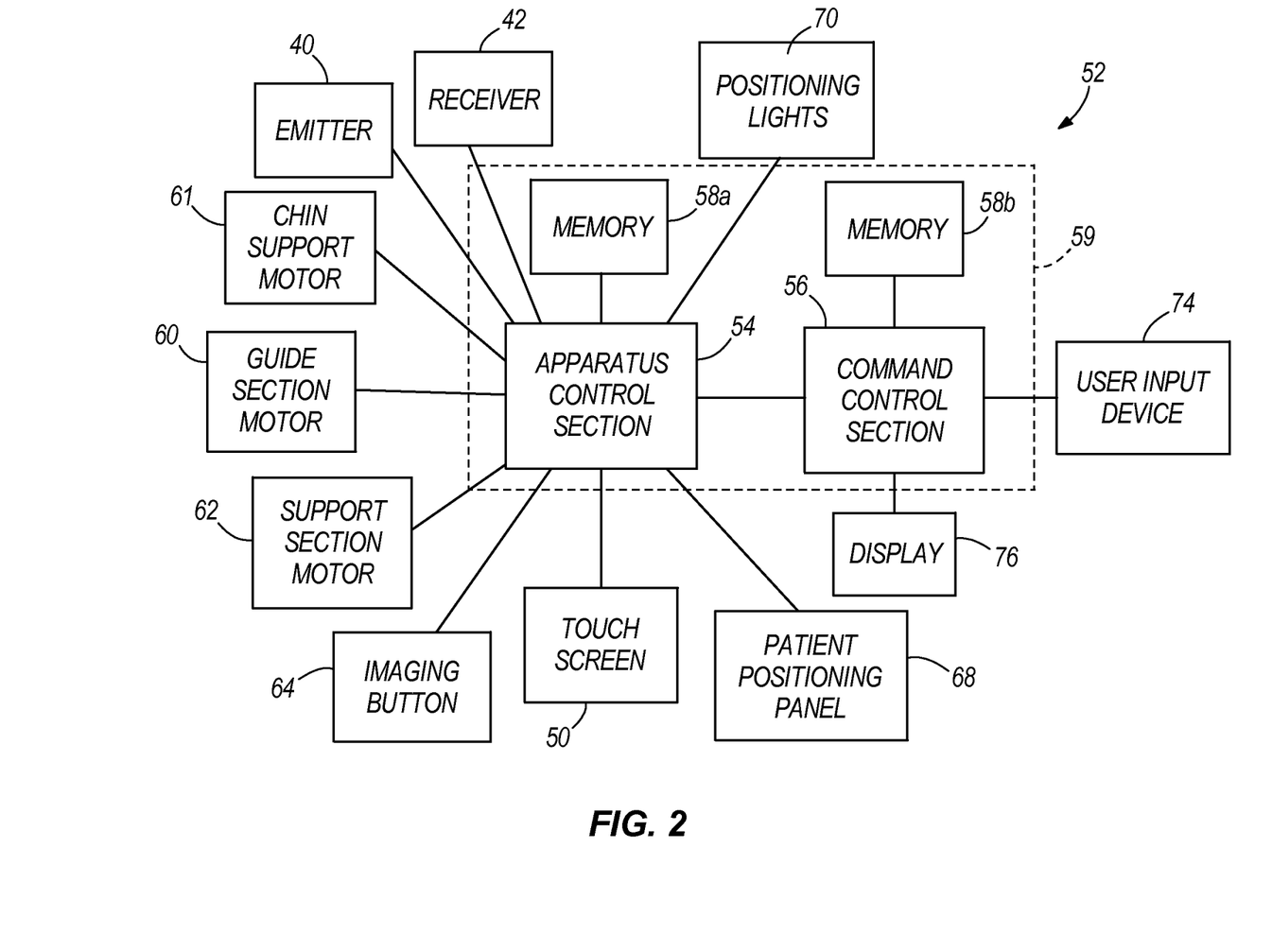
FIG. 2 is a schematic representation of portions of an exemplary X-ray imaging system.

FIG. 2 schematically depicts portions of an X-ray imaging system 52 that incorporates the X-ray imaging apparatus 20. The system 52 includes, among other things, a control circuit 59 that includes an apparatus control section 54 and a command control section 56. The apparatus control section 54 and command control section 56 each include a memory 58a, 58b, respectively. In addition, both the apparatus control section 54 and command control section 56 are programmable and can send and receive computer commands via wired or wireless links, including for example the links shown in solid-line format in FIG. 2. The command control section 56 can send electronic signals/commands to the apparatus control section 54 and can receive electronic signals/commands from the apparatus control section 54. Similarly, the apparatus control section 54 can send computer electronic signals/commands to the command control section 56 and can receive electronic signals/commands from the command control section 56. Although the example shown in FIG. 2 depicts two control sections 54, 56 that function together, alternative arrangements could include only one control section or more than two control sections that function together by sending and/or receiving commands to and from each other, respectively. The examples described in the present disclosure are not limited to the specific system 52 arrangements and configurations depicted in FIG. 2.

In the example shown in FIG. 2, the apparatus control section 54 is co-located with the X-ray imaging apparatus 20 and controls various functionalities of the X-ray imaging apparatus 20. For example, the apparatus control section 54 communicates via electronic signals/commands with the memory 58*a*; with a guide section motor 60 for causing movement of the guide section 28 along the support column 24; with a support section motor 62 for causing rotational movement of the rotating section 32; with a chin support motor 61 for causing movement of the chin support 48; and with the touch screen display 50 for displaying apparatus characteristics and functionalities and for receiving user inputs, as will be discussed further herein below. Optionally a head support motor (not shown) can also be included for causing movement of the head support 46. In addition, the apparatus control section 54 can receive commands from a user input device 64, including for example the imaging button 66 shown in FIG. 7 and from the patient positioning panel 68 shown in FIG. 4. Operation of the user input device 64 and the patient positioning panel 68 will be described further herein below.

The apparatus control section 54 also sends and receives electronic signals/commands with the emitter 40 and receiver 42 to control the emitter 40 and receiver 42 and obtain imaging data that can be converted into X-ray image(s) of the object being imaged (e.g., patient P). In use, the apparatus control section 54 receives patient positioning inputs from the patient positioning panel 68 and sends corresponding command signals to the guide section motor 60, support section motor 62, and chin support motor 61 to position the apparatus 20 with respect to the patient P. The system 20 can include more or less motors and movable sections than what is shown and described and in some examples can provide complete three-dimensional movement of the apparatus 20 with respect to the patient P. In another example, the apparatus control section 54 can receive patient positioning inputs from the patient positioning panel 68 and send corresponding command signals to move the patient P with respect to the apparatus 20, via for example a chair that is movable by a conventional chair guide motor (not shown). In a further example, the apparatus control section 54 can control the relative positioning of both the apparatus 20 and a chair guide motor to achieve a user-desired position. To facilitate easier positioning of the apparatus 20 with respect to the object being imaged, the apparatus control section 54 can also be configured to control positioning lights 70 (see e.g. FIGS. 2, 5A and 5B) for identifying on the object being imaged a field of view that is desired for imaging, as will be described further herein below.

Figure 3:
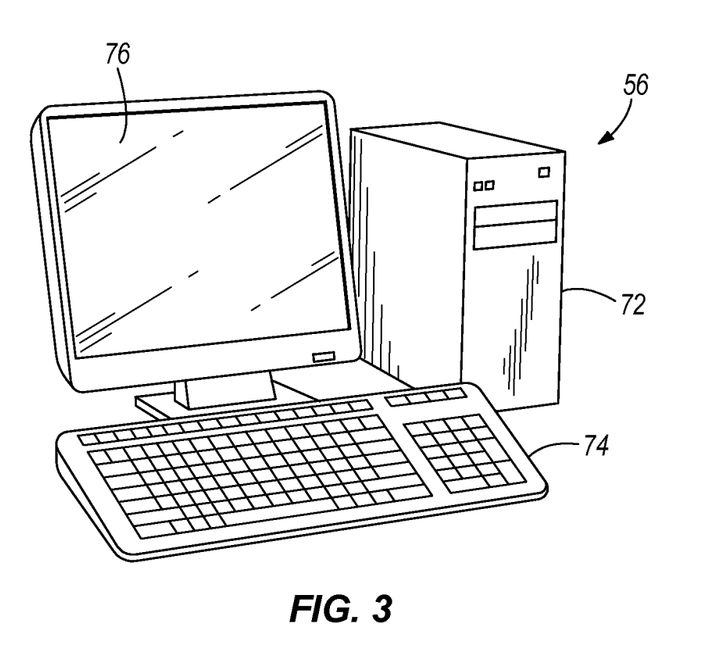
FIG. 3 is a perspective view of an exemplary command control section and display.

The apparatus control section 54 is also configured to communicate with the command control section 56, to receive electronic signals/commands from the command control section 56, and to provide image data received from the receiver 42 to the command control section 56. Referring to FIG. 3, an exemplary command control section 56 can be a personal computer 72 having a user input device 74, which in the example shown is a keyboard, and having a video display 76, which in the example shown is a computer monitor. Other types of command control sections, user input devices and displays are contemplated and are within the scope of the present disclosure. For example, the display 76 and input device 74 can instead or also comprise a touch screen device, a mouse, a handheld computer device and/or the like.

Referring to FIGS. 1A-D, 4, 5A, and 5B, a patient P is initially positioned in the apparatus 20 between the emitter 40 and receiver 42. In the example shown, the patient P is positioned with the chin on the chin support 48 and with the head on the head support 46. Next, the patient positioning panel 68 is manually operated to instruct the apparatus control section 54 to control the apparatus 20 and position the apparatus 20 into a position that is generally appropriate for X-ray imaging of the patient P. This can be done by for example the guide section motor 60, chin support motor 61, and/or support section motor 62, as described above. In the example shown in FIG. 4, pressing input key 86 turns on the positioning lights 70 as shown in FIGS. 5A and 5B, to assist in the aforementioned positioning of the patient P. FIGS. 5A and 5B depict exemplary positioning lights 70, including a midsagittal light 51 and horizontal top and bottom lights 53, 55, respectively, delineating a desired field of view for the X-ray process. Additional patient positioning lights 70 can be employed. Use of positioning lights 70 is optional and other configurations for positioning than that shown may be used. Pressing input key 88 on the patient positioning panel 68 signals the apparatus control section 54 that positioning instructions are going to be input by the user and causes the apparatus to rotate into a position for further patient positioning.

Figure 4:
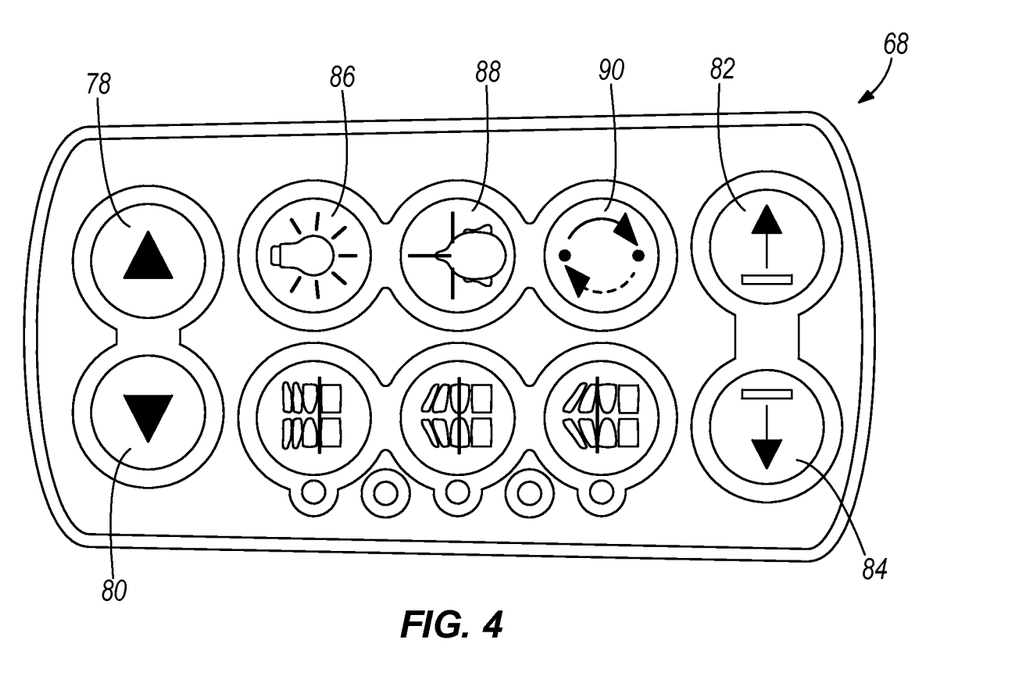
FIG. 4 is a view of a patient positioning panel.

Pressing arrows 78, 80 on the patient positioning panel 68 instructs the apparatus control section 54 to move the apparatus 20 up and down, respectively. The user can thus watch the positioning lights 70 and use the arrows 78, 80 and 82, 84 to position the lights 70 (and thus the apparatus) into an appropriate position on the patient P. Pressing input keys 78, 80 instructs the apparatus control section 54 to control the respective support section motor 62 to move the apparatus 20. Pressing arrows 82, 84 instructs the apparatus control section 54 to control the chin support motor 61 to move the chin support 48 up and down, respectively. As mentioned above, it is also recognized that instead of moving the X-ray apparatus 20, it is possible to utilize different configurations wherein for example the patient P is moved with respect to the apparatus 20 instead of or in addition to the configuration described above wherein the apparatus 20 is moved with respect to the patient P. Pressing input key 90 after imaging causes the apparatus 20 to rotate into a position where the patient can easily get out of the apparatus 20.

Figure 6:
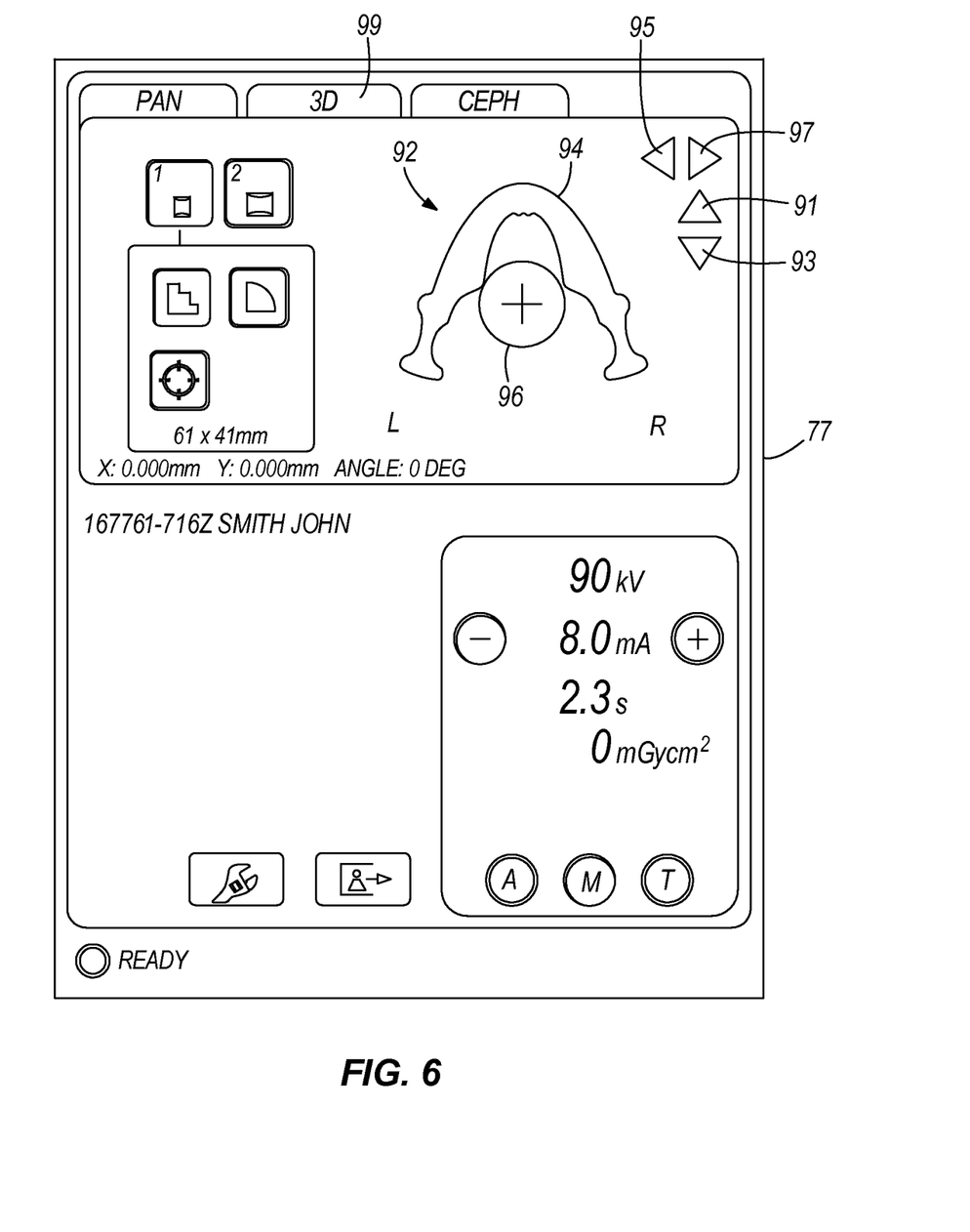
FIG. 6 is a display of an initial view of an object being imaged.

Referring to FIG. 6, once the patient P is generally positioned with respect to the apparatus 20 so as to generally achieve a desired field of view for an imaging process, for example 3-D imaging, the command control section 56 controls the video display 76 to provide a display 77 of an initial view 92 of the object, representing in this example the anatomy of the patient P to be imaged. The display 77 of the initial view 92 can also or instead be displayed on the touch screen display 50, as controlled by the apparatus control section 54, or on another display device, for example a handheld device, television screen and/or the like. In the example shown in FIG. 6, the initial view 92 includes a generic model 94 of a patient's jaw. In an alternate example, the initial view 92 can include a picture or an X-ray image of the object, for example a particular anatomy of the patient P. For example, an initial X-ray can be taken with the X-ray imaging apparatus 20 to generate the initial view 92 for viewing by the user.

In the example shown in FIG. 6, a position marker 96 is shown on the display 77. The position marker 96 has a circular shape and crosshairs; however, other configurations of the position marker may be utilized. The position marker 96 represents a particular 3-D volume that is desired for imaging. The position marker 96 overlaps the initial view 92 and is movable on the display 77 with respect to the initial view 92. In an alternate example, the initial view 92 can be movable with respect to the position marker 96. In another example, both the initial view 92 and position marker 96 can be movable with respect to each other. Relative movement of the initial view 92 and position marker 96, as described above, can be requested via the input device 74 and/or via positioning keys on a touch screen configuration, for example touch screen display 50, including for example up and down arrows 91, 93 and left and right arrows 95, 97. Other configurations for modifying the display 77 can be utilized, for example by voice commands, a mouse pad, drag-and-drop touch screen commands, and/or the like.

Input keys are also provided on the display 77 for selecting between panoramic, 3-D and cephalometric imaging modalities. The present example relates to 3-D imaging, which can be selected at input key 99; however the principles disclosed herein could be applied in other imaging modalities, as described herein above.

Figure 7:
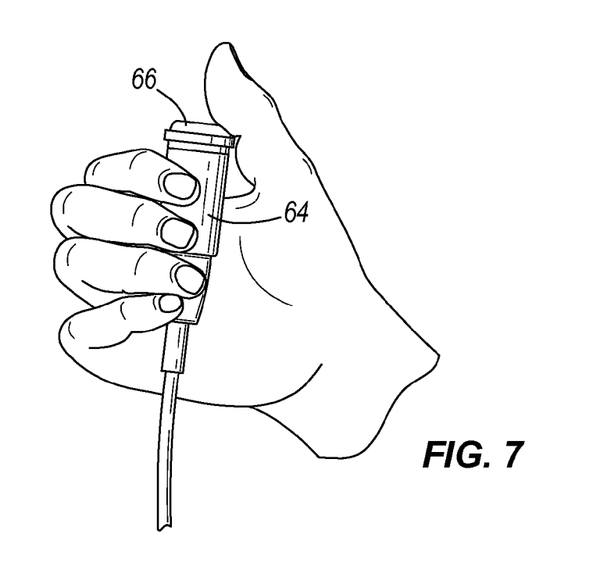
FIG. 7 is a perspective view of an input device.

Referring to FIGS. 6 and 7, the display 77, including the initial view 92, can thus be modified by the user to identify a specific area of interest on the initial view 92 of which the user desires a 3-D image. The user modifies the display 77 by moving the position marker 96 to the area of interest on the initial view 92. The user then operates the input device 64 by pressing imaging button 66, which instructs the apparatus control section 54 to control the imaging apparatus 20, including for example the guide section 28, support section 30 and rotating section 32 to move into a position with respect to the patient P that is commensurate with the location of the position marker 96 on the initial view 92. The apparatus 20 is thus positioned wherein the emitter 40 and receiver 42 operate to obtain one or more X-rays positioning images of the patient P that correspond to the relative positioning of the position marker 96 and initial view 92 on the display 77.

Thereafter, the control circuit 59 is programmed to calculate an optimal viewing angle for taking one or more preview images and transforms these angles into real world coordinates for the apparatus 20. The apparatus control section 54 then controls the imaging apparatus 20 to generate an X-ray positioning image of the patient P based upon the user modification of the initial view 92 and the calculated optimal viewing angles. One example of a positioning image provided by this process and system is provided in FIG. 8, as described herein below.

Figure 8:
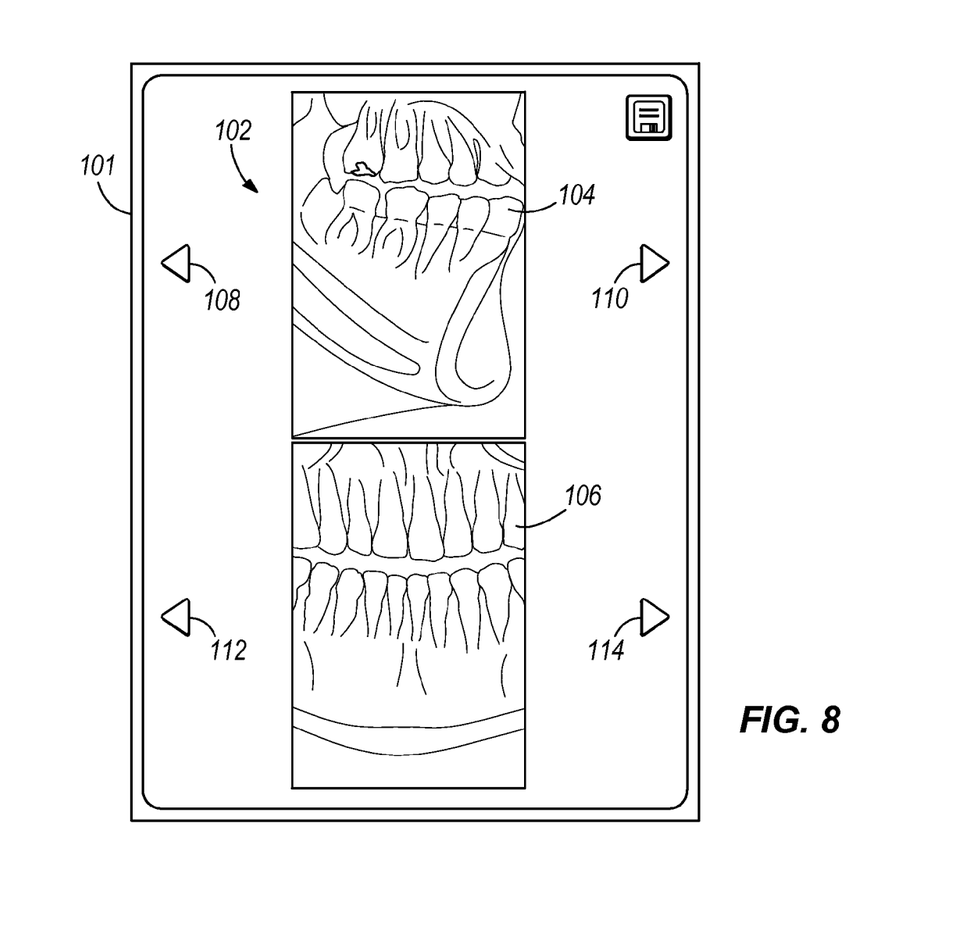
FIG. 8 is a display of positioning images of the object being imaged.

FIG. 8 depicts a display 101 displaying a positioning image 102 that is taken in accordance with the modifications of display 77, as described above. The display 101 comprises first and second X-ray images 104, 106 of the patient P taken from different angles, which in the example shown are orthogonal and tangential angles of the jaw. As with the display 77, the display 101 can be provided on for example one or both of the touch screen display 50, video display 76 and/or the like. The number of X-ray images and the angles of the X-ray images with respect to each other can vary from that shown. In the example shown, the first X-ray image 104 is a side profile of the patient's jaw. The second X-ray image 106 is a front view of the patient's jaw. The first and second X-ray images 104, 106 are thus substantially orthogonal to each other.

The X-ray images 104 and 106 are movable on the display 101. In the example shown, the X-ray images 104, 106 are also linked so that depending upon the respective angles of the X-ray images 104, 106, movement or other modification of one of the X-ray images 104, 106 on the display 101 can cause corresponding movement or modification of the other of the X-ray images 104, 106 on the display 101. The user can modify the display 101 to further identify the particular 3-D imaging volume that is desired for imaging by moving the positioning images 104 and 106 on the display 101. In this example, the user operates input keys 108, 110 for moving the first X-ray image 104 on the display 101 and input keys 112, 114 for moving the second X-ray image 106 on the display 101. The input keys 108, 110, 112, 114 can be selected by touching the touch screen display 50 or by using a mouse and cursor associated with the video display 76, and/or by other conventional input means. The display 101 can be provided with fewer or more input keys from that shown, including input keys for moving the respective images in any direction with respect to the display 101, including up and down, diagonal, and/or the like. Input keys 108, 110, 112, 114 are not required and in another example the X-ray images 104, 106 can be movable by touch screen with "drag and drop" features. Alternatively the X-ray images 104, 106 can be moved or centered on the touch screen to a location touched by the user. Other examples can be employed. As stated above, the X-ray image 104 and X-ray image 106 can be linked so that operation of one or both of the input keys 108, 110 affects the X-ray image 106 and operation of one or both of the input keys 112, 114 affects the X-ray image 104.

Once the user modifies the positioning image 102 by moving the positioning image 102 on the display 101, the input device 64 can again be operated by pressing the button 66, which instructs the apparatus control section 54 to control the imaging apparatus 20 to generate an X-ray image of the patient P, for example a 3-D image, based upon the user modification of the display 101 of the positioning image 102. Specifically, the apparatus control section 54 is programmed to control the guide section 28, support section 30 and/or rotating section 32 to reposition the imaging apparatus 20 with respect to the patient P so as to provide an X-ray image of the precise area selected on the display 101 via the user modification of the positioning image 102 described herein above. The X-ray image can be for example a 3-D image.

Figure 9:
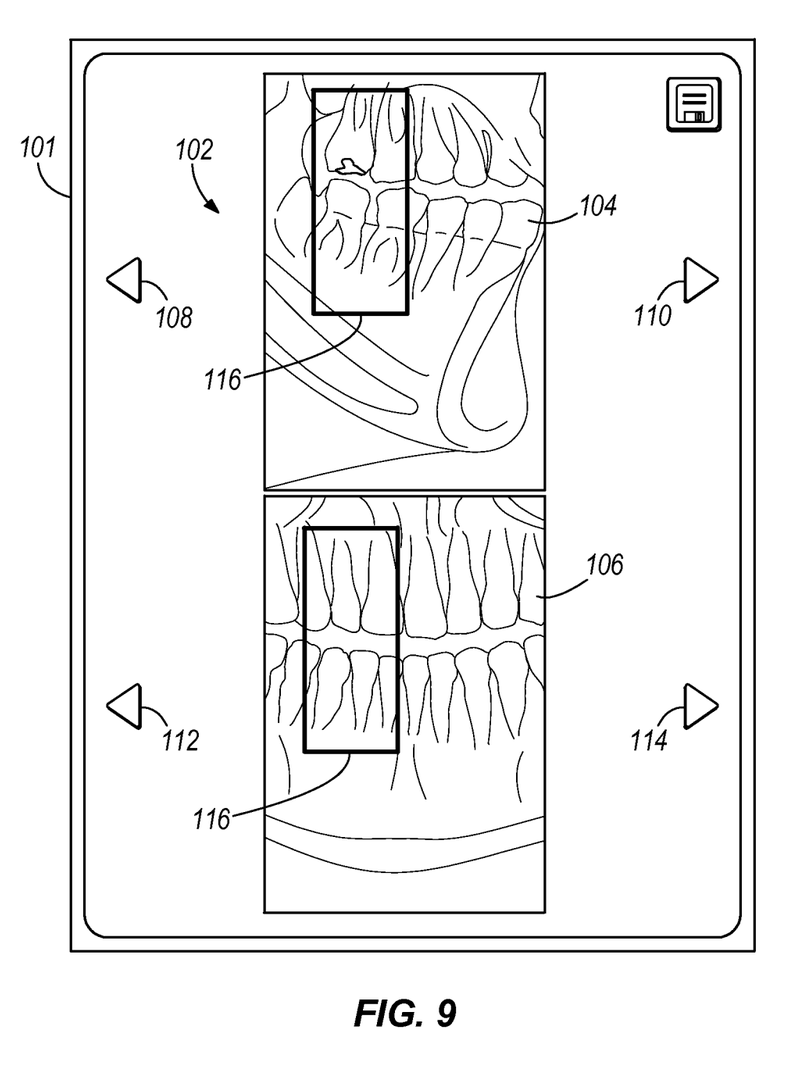
FIG. 9 is another example of a display of positioning images of the object being imaged.

In another example shown in FIG. 9, the display 101 of the positioning image 102 has a positioning position marker 116 overlapping each of the images 104, 106. At least one of the positioning image 102 and positioning position marker 116 is modifiable with respect to the other of the positioning image 102 and the positioning position marker 116. For example, the size of the positioning position marker 116 can be modified by user input to the display 101, via for example touching the touch screen display 50 or using a mouse and cursor associated with the video display 76, and/or the like. Modifying the size and position of the positioning position marker 116 can instruct apparatus control section 54 to collimate an amount of X-rays emitted through the patient P based upon the respective size of the positioning position marker 116. In another example the size of the positioning image 102 is modifiable with respect to the positioning position marker 116. Once the first and second X-ray images 104, 106 are positioned on the display 101, as described above, and the positioning position marker 116 and/or positioning image 102 is modified by the user, the input device 64 is operated by pressing imaging button 66, which instructs the apparatus control section 54 to operate the X-ray imaging apparatus 20 to generate an image, which in this example can be a 3-D X-ray image.

Figure 10:
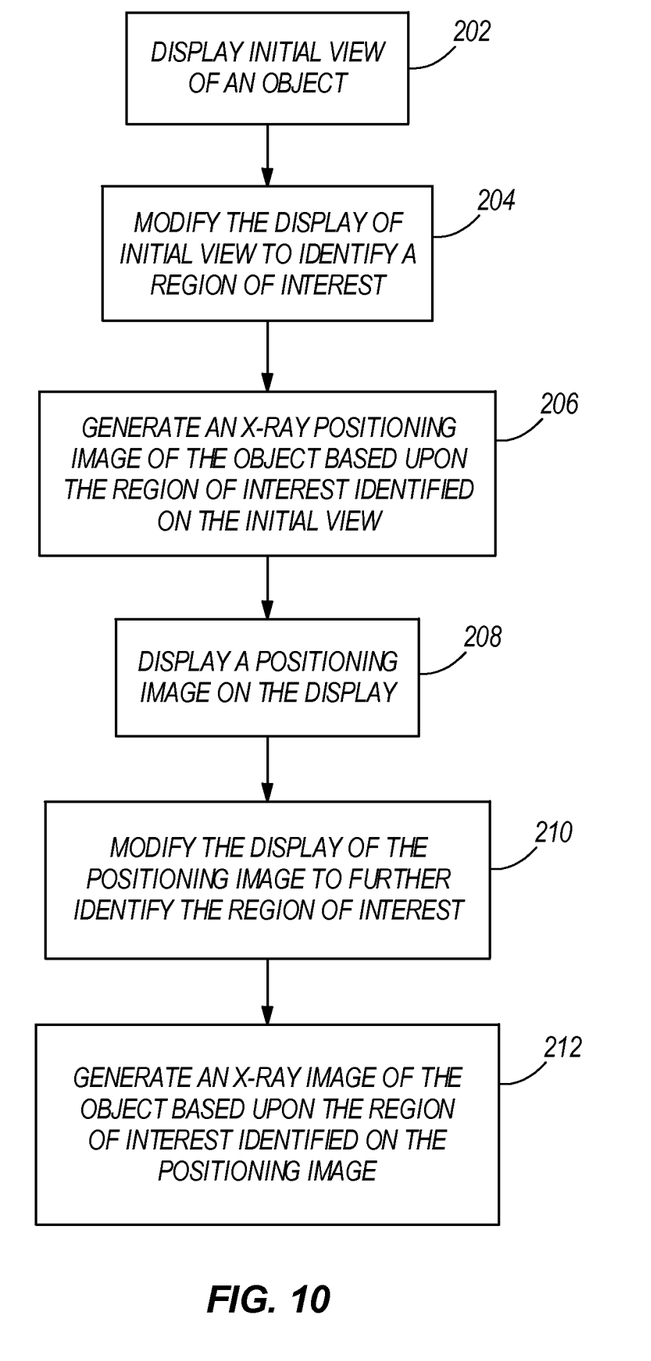
FIG. 10 is a flow chart depicting one example of a method of operating an X-ray imaging apparatus.

FIG. 10 depicts one example of a method of operating an X-ray imaging apparatus according to the present disclosure. At step 202, an initial view of an object to be imaged is displayed on a display screen. As discussed above, the initial view can be for example a generic image, a picture, an X-ray of the object, and/or the like. At step 204, a user modifies the display of the initial view to identify a region of interest for X-ray imaging. As discussed above, this can be accomplished by modifying the relative position between a positioning marker overlapping the initial view of the object. At step 206, the X-ray imaging apparatus is operated to generate an X-ray positioning image of the object based upon the region of interest identified on the initial view, as described herein above. Steps 202 and 204 are optional steps and not required. In an alternate example, the initial patient positioning can be performed with positioning lights that indicate a desired field of view. The display of an initial view can be omitted and step 206 be undertaken based on the positioning with the lights. At step 208, the imaging apparatus displays the positioning image taken at step 206 on a display. At step 210, the user modifies the display of the positioning image to further identify the region of interest. As discussed above, this can be accomplished by modifying the relative position of the positioning image on the display and/or modifying a positioning position marker with respect to the display of the positioning image. At step 212, the user operates the X-ray imaging apparatus to generate an X-ray image of the object based upon the region of interest identified on the positioning image.

Figure 11:
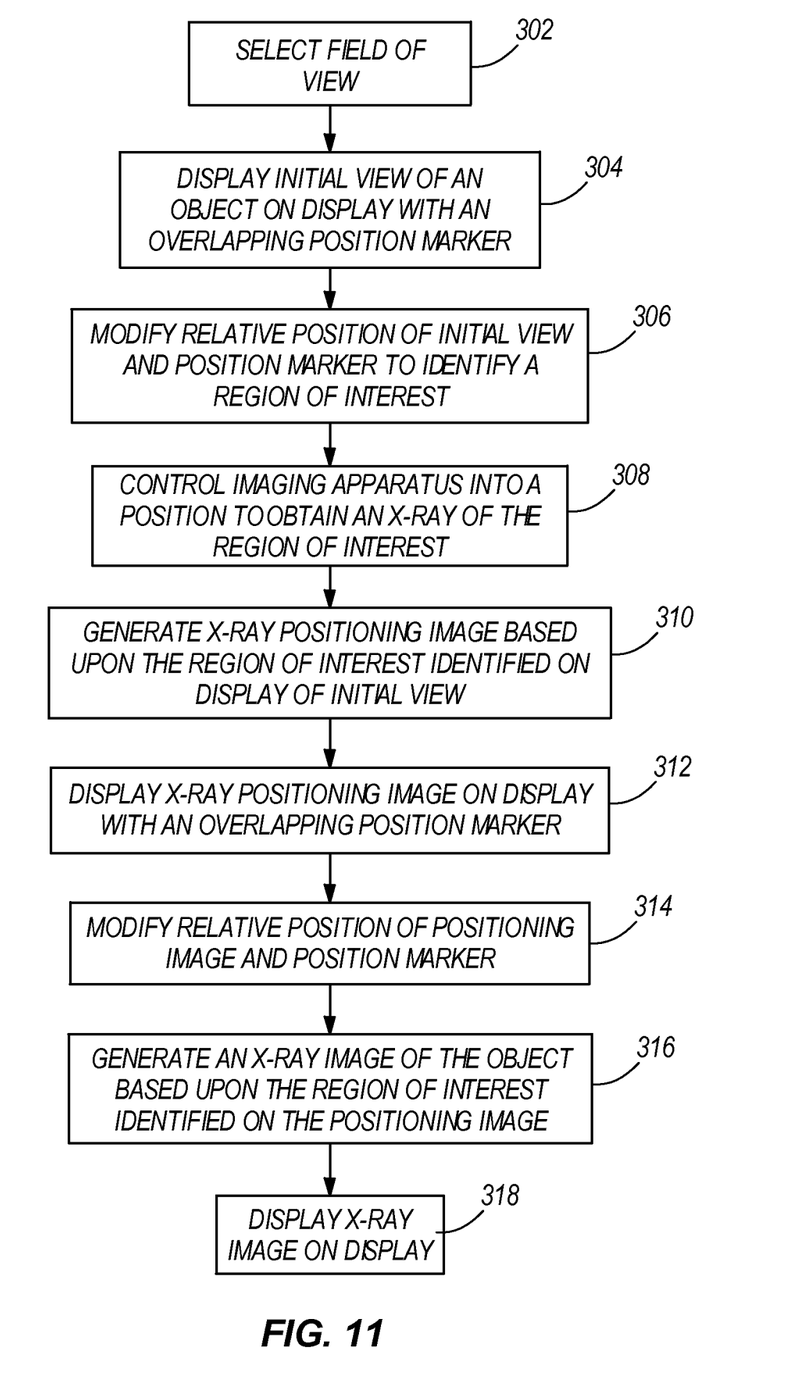
FIG. 11 is a flow chart depicting another example of a method of operating an X-ray imaging apparatus.

FIG. 11 depicts another example of a method of operating an X-ray imaging apparatus comprising an emitter emitting X-rays through an object and a receiver receiving the X-rays. The method comprises, at step 302, operating an X-ray image apparatus to select a field of view. This can include positioning the patient with respect to the imaging apparatus, and specifically with respect to the emitter and receiver. This can be facilitated by for example positioning lights, as described herein above. At step 304, the imaging apparatus is operated to display an initial view of the object to be imaged on a display with an overlapping position marker. At step 306, a user modifies the relative position and/or size of the initial view and the overlapping position marker to thereby further identify a region of interest for X-ray imaging. At step 308, the control circuit controls the imaging apparatus 20 to move into a position to obtain an X-ray of the region of interest identified by the user modification of the display. As discussed above, this can include the step of calculating optimal viewing angles for one or more X-ray positioning images. Also as discussed above, steps 304-306 can be omitted. At step 310, the X-ray imaging apparatus 20 is operated to generate an X-ray positioning image based upon the region of interest identified on the display of the initial view. At step 312, the X-ray imaging apparatus is operated to display the X-ray positioning images with an overlapping position marker. At step 314, the X-ray positioning image is modified by modifying relative position and/or size of the positioning image and positioning marker. At step 316, the X-ray imaging apparatus is operated to generate an X-ray image of the object based upon the region of interest identified on the positioning image. At step 318, the X-ray imaging apparatus is operated to display the X-ray image on a display.

As will be understood by those having ordinary skill in the art, the present disclosure thus provides examples of X-ray imaging systems that comprise an imaging apparatus having an emitter emitting X-rays through an object and a receiver receiving the X-rays, and a control circuit controlling the emitter and processing the X-rays received by the receiver to generate X-ray images of the object. Specific examples of the imaging apparatus and control circuit are described with reference to the attached drawing figures. These examples are not limiting and the concepts of the present disclosure are applicable to other types of imaging apparatus having different configurations of control circuitry. In examples discussed herein, the control circuit controls a display to display an initial view of the object that is modifiable by a user. The control circuit controls the imaging apparatus to generate an X-ray positioning image of the object based upon a user modification of the display of the initial view. The control circuit further controls the display to display the positioning image, which is modifiable by a user. The control circuit also controls the imaging apparatus to generate an X-ray image of the object based upon a user modification of the display of the positioning image. In certain examples, a position marker overlaps the initial view and at least one of the initial view and position marker is movable on the display with respect to the other of the initial view and position marker. The control circuit can optionally be configured to control the imaging apparatus to generate the positioning image based upon the relative position and/or size of the initial view and position marker.

In the examples shown, the positioning image includes a plurality of X-ray images that are taken from different angles. These images are linked so that modification of one of the plurality of X-ray images on the display can cause corresponding modification of the rest of the plurality of X-ray images. Modification can include for example movement. These examples are not limiting however and different numbers and orientations of images can be employed to achieve the objectives described in the present disclosure.

In further examples, a position marker overlaps the positioning image and is modifiable with respect to the positioning image so that the control circuit can control the imaging apparatus to generate the X-ray image based upon a relative modification of the positioning image and positioning position marker. For example, the modification can comprise a change in size of the positioning position marker. Based upon this change in size, the control circuit can be configured to collimate an amount of X-rays emitted through the object.

The present disclosure thus provides means for controlling the emitter and processing X-rays received by the receiver to generate X-ray images of the object that are more accurate and that require comparatively less radiation emitted to the object being imaged. Means for controlling a display to display an initial view of the object that is modifiable by a user, means for controlling the imaging apparatus to generate an X-ray positioning image based upon the modification of the initial view, and means for controlling the display to display a positioning image that is modifiable by the user are also disclosed herein. The imaging apparatus is thus controlled to generate an X-ray image of the object based upon a user modification of the display of the positioning image, thus achieving a more precise view of the area of interest and requiring less radiation emitted to the patient. Corresponding methods of operating the apparatus described herein above are also disclosed.

What is claimed is:
1. An X-ray imaging system, comprising:
an imaging apparatus comprising an emitter adapted to emit X-rays through an object and a receiver receiving the X-rays; and a control circuit adapted to control the emitter and process the X-rays received by the receiver to generate X-ray images of the object;

wherein the control circuit is adapted to control the imaging apparatus to generate an X-ray positioning image of the object;

wherein the control circuit is adapted to control a display to display the positioning image, the display of the positioning, image being modifiable by a user; and wherein the control circuit is adapted to control the imaging apparatus to generate an X-ray image of the object based upon a user modification of the display of the positioning image.

2. A system according to claim 1, wherein the control circuit is adapted to control the display to display an initial view of the object and a position marker overlapping the initial view, wherein at least one of the initial view and position marker is movable on the display by a user with respect to the other of the initial view and position marker; and wherein the control circuit is adapted to control the imaging apparatus to generate the positioning image based upon a relative position or size of the initial view and position marker.

3. A system according, to claim 1, wherein the positioning image is movable on the display and the control circuit is adapted to control the imaging apparatus to generate the X-ray image based upon the position or size of the positioning image on the display.

4. A system according to claim 1, wherein the positioning image comprises a plurality of X-ray images of the object from different angles.

5. A system according to claim 4, wherein the plurality of X-ray images are linked so that modification of one of the plurality of X-ray images on the display causes corresponding modification of the rest of the plurality of X-ray images on the display.

6. A system according, to claim 5, wherein the modification comprises a movement.

7. A system according to claim 5, wherein the plurality of X-ray images comprises two X-ray images.

8. A system according to claim 7, wherein the two X-ray images are orthogonal to each other.

9. A system according to claim 1, comprising a positioning position marker overlapping the positioning image, wherein at least one of the positioning image and positioning position marker is modifiable with respect to the other of the positioning image and the positioning position marker, and wherein the control circuit is adapted to control the imaging apparatus to generate the X-ray image based upon a relative modification of the positioning image and positioning position marker.

10. A system according to claim 9, wherein the modification comprises a change in size of the positioning position marker.

11. A system according to claim 10, wherein the control circuit is adapted to control the system to collimate an amount of X-rays emitted though the object based upon at least one of the size and position of the positioning position marker.

12. A system according to claim 1, comprising an input device adapted to cause the control circuit to control the imaging apparatus to generate the positioning image.

13. A system according to claim 12, wherein the control circuit is adapted to control a relative position of the object and the X-ray apparatus when the input device is actuated to cause the control circuit to generate the positioning image.

14. A system according to claim 1, comprising an input device adapted to cause the control circuit to control the imaging apparatus to generate the X-ray image.

15. A system according to claim 14, wherein the control circuit is adapted to control a relative position of the object and the X-ray apparatus when the input device is actuated to cause the control circuit to control the imaging apparatus to generate the X-ray image.

16. A system according to claim 1, comprising the display.

17. A method of operating an X-ray imaging apparatus comprising an emitter emitting X-rays through an object and a receiver receiving the X-rays, the method comprising:

displaying an initial view of the object on a display;

modifying the display of the initial view to identify a region of interest;

operating, via the control circuit, the emitter and receiver to generate an X-ray positioning, image of the object based upon the region of interest identified on the display of the initial view;

displaying the positioning image on the display;

modifying the display of the positioning image to further identify the region of interest; and operating, via the control circuit, the emitter and receiver to generate an X-ray image of the object based upon the region of interest identified on the positioning image.

18. A method according to claim 17, comprising identifying the region of interest on the display of the initial view by modifying a relative position of the initial view and a position marker overlapping the initial view.

19. A method according to claim 17, comprising identifying the region of interest on the positioning image of the display by modifying a position or site of the positioning image on the display.

20. A method according to claim 17, wherein the positioning image comprises a plurality of X-ray images of the object from different angles.

21. A method according to claim 18, wherein the plurality of X-ray images are linked so that movement of one of the plurality of X-ray images on the display causes corresponding movement of the rest of the plurality of X-ray images on the display.

22. A method according to claim 19, wherein the plurality of X-ray images comprises two X-ray images.

23. A method according to claim 22, wherein the two X-ray images are orthogonal to each other.

24. A method according to claim 17, comprising further identifying the region of interest on the positioning image of the display by modifying a relative position or size of the positioning image and a position marker overlapping the positioning image.

25. A method according to claim 24, comprising modifying the size of the position marker with respect to the positioning image.

26. A method according to claim 25, comprising adjusting, via the control circuit, the amount of X-rays emitted though the object based upon the size of the positioning position marker.

27. A method according to claim 17, comprising operating an input device to cause the control circuit to control the imaging apparatus to generate the positioning image based upon the position or size of the initial view and position marker.

28. A method according to claim 27, wherein the control circuit controls a relative position between the object and the X-ray apparatus when the input device is actuated to cause the control circuit to generate the positioning image.

29. A method according to claim 17, comprising operating an input device to cause the control circuit to control the imaging apparatus to generate an X-ray image of the object based upon the position or size of the positioning image on the screen.

30. A method according to claim 29, wherein the control circuit controls a relative position or size of the object and the X-ray apparatus when the input device is actuated to cause the control circuit to control the imaging apparatus to generate the X-ray image.

31. An X-ray imaging system, comprising:
  an imaging apparatus comprising an emitter adapted to emit X-rays through an object and a receiver receiving the X-rays; and
  a control circuit is adapted to control the emitter and process the X-rays received by the receiver to generate X-ray images of the object;
  wherein the control circuit is adapted to control the imaging apparatus to generate an X-ray positioning image of the object;
  wherein the control circuit controls the display to display the positioning image, the display of the positioning image being modifiable by a user;
  wherein the positioning image comprises a plurality of X-ray images of the object from different angles;
  wherein the plurality of X-ray images are linked such that modification of one of the plurality of X-ray images on the display causes corresponding modification of the rest of the plurality of X-ray images on the display; and
  wherein the control circuit is adapted to control the imaging apparatus to generate an X-ray image of the object based upon a user modification of the display of the positioning image.

32. An X-ray imaging system according to claim 31, comprising a positioning position marker overlapping the positioning image, wherein at least one of the positioning image and positioning position marker is modifiable with respect to the other of the positioning image and the positioning position marker, and wherein the control circuit is adapted to control the imaging apparatus to generate the X-ray image based upon a relative modification of the positioning image and positioning position marker.

* * * * *